(12) United States Patent
Bahn et al.

(10) Patent No.: US 9,855,253 B2
(45) Date of Patent: Jan. 2, 2018

(54) **PHARMACEUTICAL COMPOSITION CONTAINING FK506 DERIVATIVE FOR TREATING FUNGAL INFECTION CAUSED BY GENUS *CRYPTOCOCCUS* AND GENUS *CANDIDA* AND USE THEREOF**

(71) Applicant: INTRON BIOTECHNOLOGY CO., LTD., Gyeonggi-do (KR)

(72) Inventors: Yong Sun Bahn, Seoul (KR); Hyo Jeong Kwon, Seoul (KR); Yeo Joon Yoon, Seoul (KR); Yeon Hee Ban, Seoul (KR)

(73) Assignee: INTRON BIOTECHNOLOGY CO., LTD., Gyeonggi-do (KR)

( * ) Notice: Subject to any disclaimer, the term of this patent is extended or adjusted under 35 U.S.C. 154(b) by 11 days.

(21) Appl. No.: 15/320,189

(22) PCT Filed: Jun. 29, 2015

(86) PCT No.: PCT/KR2015/006635
§ 371 (c)(1),
(2) Date: Dec. 19, 2016

(87) PCT Pub. No.: WO2016/003135
PCT Pub. Date: Jan. 7, 2016

(65) Prior Publication Data
US 2017/0135993 A1    May 18, 2017

(30) Foreign Application Priority Data
Jun. 30, 2014    (KR) .................. 10-2014-0080473

(51) Int. Cl.
*A61K 31/436* (2006.01)
*A61K 31/407* (2006.01)

(52) U.S. Cl.
CPC .......... *A61K 31/436* (2013.01); *A61K 31/407* (2013.01)

(58) Field of Classification Search
CPC ........................... A61K 31/436; A61K 31/407
USPC ........................................................ 514/291
See application file for complete search history.

(56) References Cited

FOREIGN PATENT DOCUMENTS

| KR | 10-20050071491 A | 3/2005 |
|----|------------------|--------|
| KR | 10-20040010919 B1 | 9/2005 |

OTHER PUBLICATIONS

Odom et al, Antimicrobial Agents and Chemotherapy (1997), vol. 41(1), pp. 156-161.*
Wong et al, The Journal of Antibiotics (1998), vol. 51(5), pp. 487-491.*

(Continued)

*Primary Examiner* — Kathrien Cruz
*Assistant Examiner* — Janet L Coppins
(74) *Attorney, Agent, or Firm* — Yakov S. Sidorin; Quarles & Brady LLP

(57) ABSTRACT

The present invention relates to a pharmaceutical composition containing FK506 derivative for treating a fungal infection caused by the genus *Cryptococcus* or the genus *Candida*, and a use thereof. In addition, the present invention relates to a therapeutic agent for fungal infection caused by the genus *Cryptococcus* or the genus *Candida*, the therapeutic agent containing FK506 derivative. The pharmaceutical composition of the present invention is harmless to the human body, and can make a great contribution to providing antifungal drugs with an excellent antifungal effect.

6 Claims, 3 Drawing Sheets

(56) References Cited

OTHER PUBLICATIONS

Steinbach, William J., et al., "In Vitro Interactions Between Antifungals and Immunosuppressants Against Aspergillus fumigatus," Antimicrobial Agents and Chemotherapy, May 2004, pp. 1664-1669.
Chen, Dandan, et al., "FK506 Maturation Involves Cytochrome P450 Protein-Catalyzed Four-Electron C-9 Oxidation in Parallel with a C-31 O-Methylation," Journal of Bacteriology, May 2013, vol. 195, No. 9, pp. 1931-1939.
Nim, Shweta, et al., "FK520 Interacts with the Discrete Intrahelical Amino Acids of Multidrug Transporter Cdr1 Protein and Acts as Antagonist to Selectively Chemosensitive Azole-Resistant Clinical Isolates of Candida Albicans," Federation of European Microbiological Societies, Mar. 2014, vol. 14, pp. 624-632.
Shafiee, Ali., et al., "Chemical and Biological Characterization of Two FK506 Analogs Produced by Targeted Gene Disruption in *Streptomyces* sp. MA6548," The Journal of Antibiotics, May 1997, pp. 418-423.
International Search Report, dated Sep. 16, 2015, in related Korean International Application No. PCT/KR2015/006635, 2 pages.

* cited by examiner

[Figure 1]
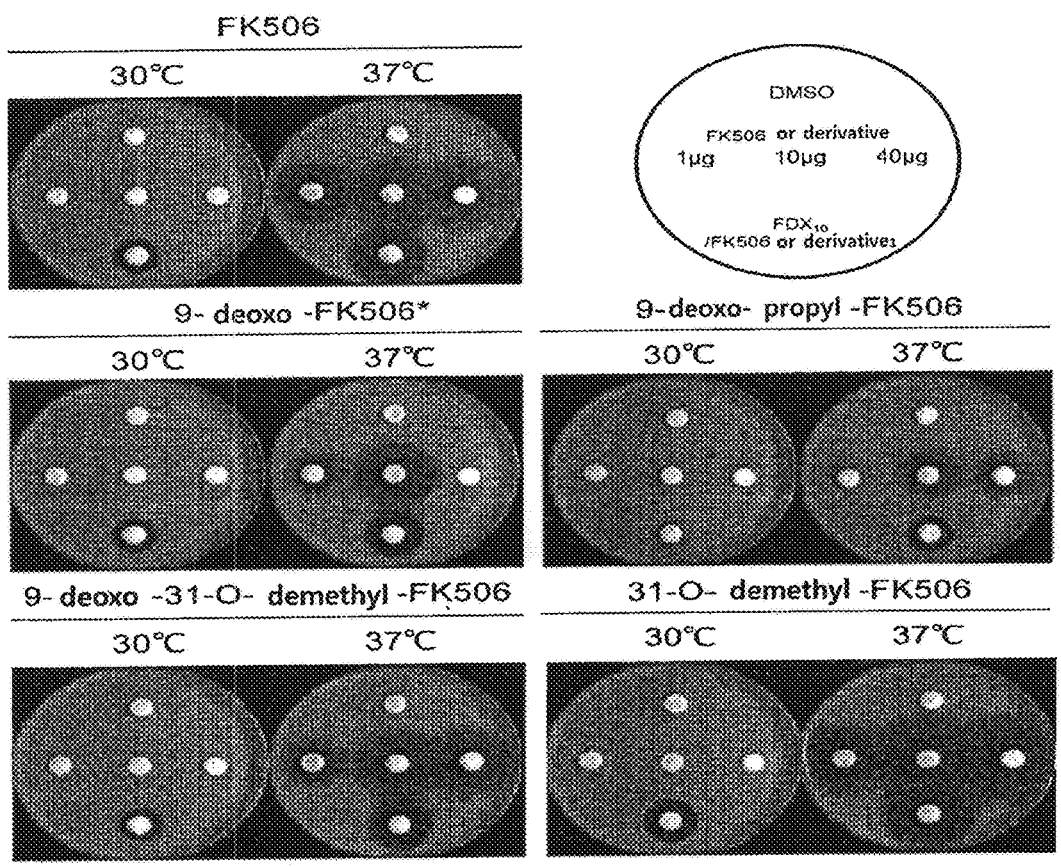

[Figure 2]
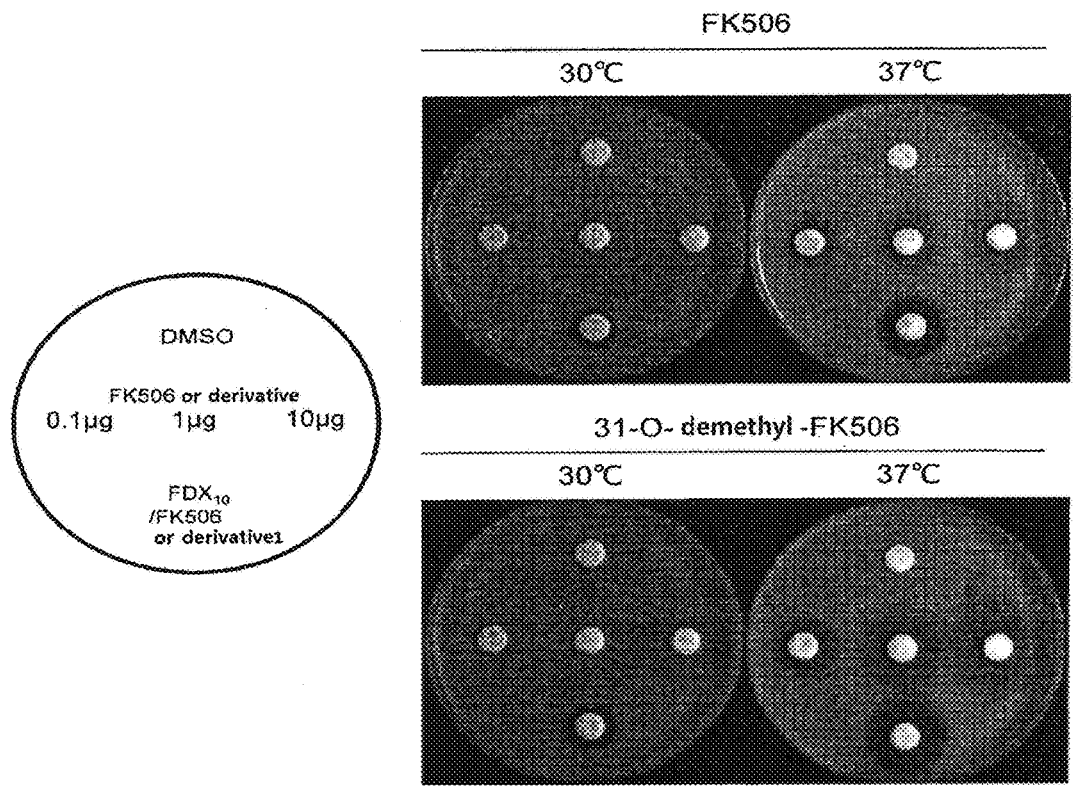

[Figure 3]
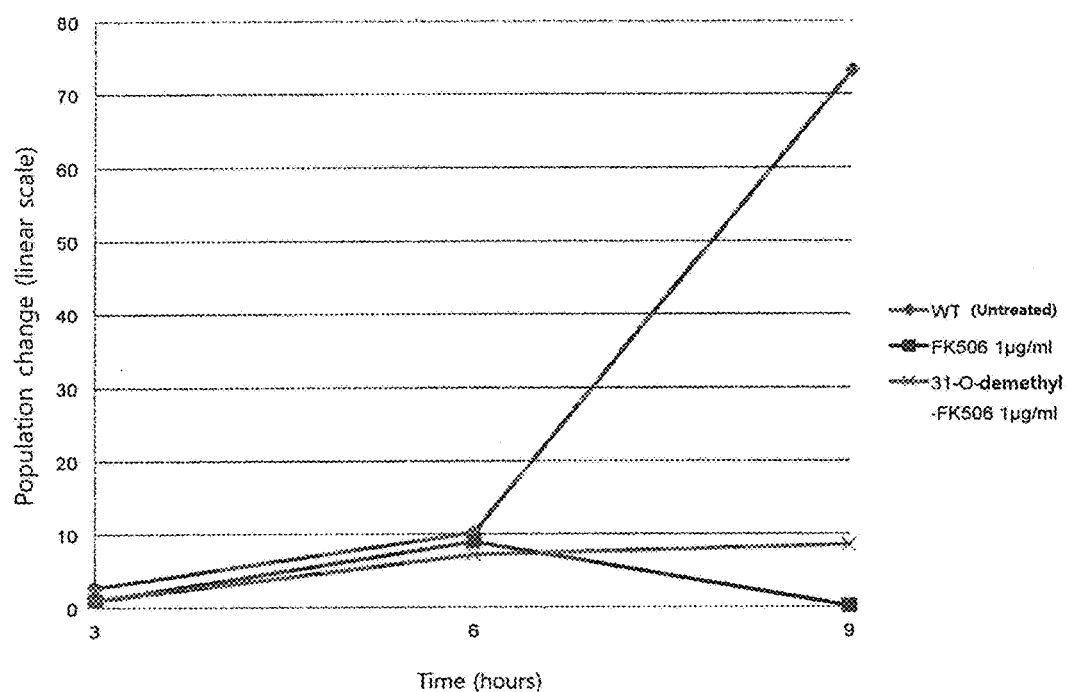

PHARMACEUTICAL COMPOSITION CONTAINING FK506 DERIVATIVE FOR TREATING FUNGAL INFECTION CAUSED BY GENUS *CRYPTOCOCCUS* AND GENUS *CANDIDA* AND USE THEREOF

CROSS-REFERENCE TO RELATED APPLICATIONS

This application represents the national stage entry of PCT International Application No. PCT/KR2015/006635 filed Jun. 29, 2015, which claims priority of Korean Patent Application No. 10-2014-0080473 filed Jun. 30, 2014, the disclosures of which are incorporated by reference here in their entirety for all purposes.

TECHNICAL FIELD

The present invention relates to a pharmaceutical composition for treating fungal infections caused by a fungus of the genus *Cryptococcus* and a fungus of the genus *Candida* the pharmaceutical composition containing FK506 derivative, and to the use thereof.

BACKGROUND ART

Fungal infectious diseases in humans and animals can be largely classified into two types depending on the position of infected tissue: systemic mycoses, and dermatomycoses. Among them, systemic mycoses include cryptococcosis, candidasis, aspergillosis, etc., which do not frequently occur in healthy persons, but frequently occur in persons with weak immunity. Cryptococcosis is caused by infection with *Cryptococcus neoformans* which infects all parts (including skin) of patients with low immunity, such as AIDS patients, and particularly, infects the brain and meninges to cause meningitis, brain abscess and brain tumor. Candidasis is mycosis caused by *Candida albicans*, and was first isolated from an oral thrush patient. Moreover, Candidasis causes vaginitis in women and causes diaper rash in infants.

In recent years, with the increase in the number of immunocompromised patients by anticancer chemotherapy or administration of immunosuppressants after organ transplantation or in the number of AIDS patients, the incidence of systemic fungal infections has greatly increased, and the severity thereof also has increased day by day. In fact, cancer or AIDS patients die of the fungal infection of their organs or blood rather than the disease itself. Furthermore, fungi that cause fungal infections have been progressively diversified, and it is expected that much more kinds of fungi will cause invasive infections.

Antifungal agents that are currently used in clinical practice are mostly azole-based compounds in addition to amphotericin B. However, such antifungal agents have the disadvantage of causing severe side effects when being used.

Commercially available antifungal agents have various disadvantages, including toxicity, a narrow spectrum of activity, and fungistatic rather than fungicidal nature. Some of these antifungal agents also show drug-drug interactions that make treatment very complex. In recent years, as fungal infection in immunosuppressive patients has frequently occurred and the population of these patients has increased steadily, there has been an increasing demand for new antifungal agents having broad-spectrum activity and excellent pharmacological properties.

Meanwhile, FK506 was isolated as a metabolite of *Streptomyces tsukabaensis* by the Fujisawa research group (Japan) in 1984. In 1989, a clinical trial using FK506 for liver transplantation was initiated. FK506 is 50-100 times stronger in efficacy than Cyclosporine A while it is comparable to Cyclosporine A in tex-ms of toxicity or side effects. Merck (USA) has conducted studies to modify the structure of FK506 in order to reduce the toxicity thereof, and the mechanism of action and functions of FK506 were considerably revealed during such studies.

Functionally, FK506 can be divided into three regions: the KFBP-binding domain, the calcineurin-binding domain, and the northwest region. The intermolecular interactions between FK506 and FKBP12 molecules are mostly hydrophobic, and only four intermolecular hydrogen bonds are formed between the two molecules. It is known that, as FK-506 and FKBP-12 bind more potently, they gain a greater affinity for calcineurin. Such increased affinity then leads to greater immunosuppressive activity. The northwest region of FK506 does not interact with FKBP12 or calcineurin.

FK506 has been used as therapeutic agents against organ or tissue transplantation rejection, graft-versus-host responses, atopic dermatitis, allergic contact dermatitis, lichen planus mucosae, and pyoderma gangrenosum. In recent years, other functions of FK506 have been found. For example, the literature [Sulaiman O A, et al., Exp Neurol 2002 May, 175(1): 127-37] describes that FK506 promotes the regeneration of peripheral nerve.

Korean Patent Application Publication No. 10-2004-0010919 (entitled "A method for inhibiting cellular aging using FK506 or a derivative thereof and a culture medium") discloses a method of inhibiting cellular aging, extending cell life and increasing cell growth in culture by use of FK506 or a derivative thereof.

In addition, Korean Patent Application Publication No. 10-2005-0071491 (entitled: Use of tacrolimus derivatives combined with β2-agonists for the treatment of asthma") discloses a new use of FK506 derivatives and β2-agonist for manufacturing a medicament for simultaneous, separate or sequential use for treating or preventing acute or chronic asthma.

However, the use of FK506 derivatives for treating a fungal infection caused by a fungus of the genus *Cryptococcus* or a fungus of the genus *Candida* has not yet been reported.

THE DETAILED DESCRIPTION OF THE INVENTION

Technical Problem

Accordingly, the present inventors have found a novel use of FK506 derivatives having antifungal activity against a fungal infection caused by a fungus of the genus *Cryptococcus* or a fungus of the genus *Candida*.

Therefore, an object of the present invention is to provide a pharmaceutical composition for treating a fungal infection caused by a fungus of the genus *Cryptococcus* or a fungus of the genus *Candida*, the pharmaceutical composition containing FK506 derivative.

Another object of the present invention is to provide an agent for treating a fungal infection caused by a fungus of the genus *Cryptococcus* or a fungus of the genus *Candida*, the agent containing FK506 derivative.

Means to Resolve Technical Problem

To achieve the problem above, one embodiment of the present invention provides a novel use of FK506 derivative as a pharmaceutical composition for treating a fungal infection caused by a fungus of the genus *Cryptococcus* or a fungus of the genus *Candida*, the pharmaceutical composition containing FK506 derivative.

Another embodiment of the present invention provides a novel use of FK506 derivative as an agent for treating a fungal, infection caused by a fungus of the genus *Cryptococcus* or a fungus of the genus *Candida*, the agent containing FK506 derivative.

Effects of the Invention

The present invention provides a pharmaceutical composition for treating a fungal infection caused by a fungus of the genus *Cryptococcus* or a fungus of the genus *Candida*, the pharmaceutical composition containing FK506 derivative. The pharmaceutical composition has advantages in that it is harmless to the human body and has excellent antifungal effects.

BRIEF DESCRIPTION OF DRAWINGS

FIGS. 1 and 2 are images showing the inhibitory activity of a composition according to one embodiment of the present invention against *Cryptococcus neoformans*.

FIG. 3 is a graph showing the inhibitory activity of a composition according to one embodiment of the present invention against *Candida albicans* as a function of time.

BEST MODE TO IMPLEMENT THE INVENTION

Hereinafter, embodiments of the present invention will be described in detail. It is to be understood, however, that these embodiments are only for illustrative purposes only and are not intended to limit the scope of the present invention. Furthermore, various modifications and applications are possible without departing from the spirit and scope of the present invention as defined in the appended claims and equivalents thereof.

In one embodiment, the present invention provides a pharmaceutical composition for treating a fungal infection caused by a fungus of the genus *Cryptococcus* or a fungus of the genus *Candida*, the pharmaceutical composition containing FK506 derivative.

The fungus of the genus *Cryptococcus* may be *Cryptococcus neoformans* or *Cryptococcus gattii*, and the fungus of the genus *Candida* may be *Candida albicans*.

The antifungal composition according to the present invention may contain the FK506 derivative alone, and may further contain a pharmacologically acceptable carrier in addition. The FK506 derivative is preferably 31-O-demethyl-FK506, 9-deoxo-FK506, 9-deoxo-31-O-demethyl-FK506 or 9-deoxo-propyl-FK506, more preferably 31-O-demethyl-FK506. In addition, the effect of the pharmaceutical composition on the treatment of the fungal infection increases proportionally to the content of the FK506 derivative in the pharmaceutical composition of the present invention. Specifically, the pharmaceutical composition of the present invention preferably contains the FK506 derivative at a concentration of 1 µg/ml to 100 µg/ml, more preferably 10 µg/ml to 40 µg/ml. However, the content of the FK506 derivative in the pharmaceutical composition is not limited thereto, and can be suitably adjusted depending on the administration mode and intended use of the pharmaceutical composition.

The pharmacologically acceptable carrier may be a substance such as an excipient or a diluent, which is contained in conventional antifungal agents, and examples thereof include, but are not limited to, saline, buffered saline, dextrose, isoparaffini, water, glycerol and ethanol.

The formulation of the antifungal pharmaceutical composition can be suitably determined depending on the administration mode and intended use of the composition, and may be in the form of, for example, solution, suspension, granules, plaster, aromatic water, powder, syrup, aerosol, extract, ointment, fluid extract, emulsion, decoction, infusion, eye drop agent, tablet, injectable solution, spirit, capsule, cream or pill.

The pharmaceutical composition may be used as a cleaning agent, a drug, a food additive, an aromatic agent or a cosmetic agent to inhibit the production and growth of pathogenic bacteria or fungi that produces toxins. If the pharmaceutical composition is used as a cleaning agent, it may be prepared as a spray agent, a washing agent, shampoo, rinse or soap, etc. If the pharmaceutical composition is used as a food additive, the formulation thereof can, be suitably determined depending on the kind and intended use of food. If the pharmaceutical composition is used as an aromatic agent, it may further comprise a volatile substance.

In another embodiment, the present invention provides an agent for treating a fungal infection caused by a fungus of the genus *Cryptococcus* or a fungus of the genus *Candida*, the agent containing FK506 derivative.

Herein, FK506 derivatives are as described above. The agent for treating the fungal infection according to the embodiment of the present invention is harmless to the human body and has excellent antifungal effects, and thus can be effectively used for the treatment of a fungal infection caused by a fungus of the genus *Cryptococcus* or a fungus of the genus *Candida*, wherein the agent contains FK506 derivative.

Hereinafter, the present invention will be described in further detail with reference to examples. However, the scope of the present invention is not limited to these examples.

Example: Antifungal Activities of FK506 Derivatives

The antifungal activities of FK506 derivatives against fungi such as *Cryptococcus neoformans* and *Candida albicans*, which are human pathogenic yeasts, were analyzed by the standard agar diffusion method (Murray et al., 1995 Manual of clinical microbiology ($6^{th}$ ed.), Washington, ASM Press, pp. 1275-1294), 100 µL of a standardized inoculam containing $10^7$ CFU/ml, of a fungal suspension was uniformly plated in a Petri dish containing 20 mL of potato-dextrose agar (PDA) medium, and was dried for 5 minutes. A sterilized Whatman No. 1 filter paper disk baying a diameter of 6 mm was wet with each of 0.1 µg, 1 µg, 10 µg and 40 µg/ml of FK506 derivative dissolved in the same solvent as that used for extraction. As a control, an untreated disk and a disk wet with FK506 were used. Each plate was incubated at 30° C. and 37° C. for 2-3 days, and then the antifungal activity of each FK506 derivative was evaluated by comparing the diameters of inhibition zones against *Cryptococcus neoformans* and *Candida albicans*. The experiment for analysis of the antifungal activity was repeated at least three times.

Table 1 below shows the results obtained by treating *Cryptococcus neoformans* with 10 µg/ml of each of FK506 and derivatives represented by the following formulas (I) to (IV) and confirming the antifungal activity of each derivative. The diameters of the inhibition zones are shown in units of mm.

As can be seen in Table 1 below, the FK506 derivatives very effectively inhibited *Cryptococcus neoformans* which is a human pathogenic yeast.

TABLE 1

| Kind of test fungus | Untreated | FK506 | Derivative of Formula (I) | Derivative of Formula (II) | Derivative of Formula (III) | Derivative of Formula (IV) |
|---|---|---|---|---|---|---|
| *Cryptococcus neoformans* | 0 | 16.8 | 26.4 | 21.6 | 21.6 | 15.6 |

31-O-demethyl-FK506, 9-deoxo-FK506, 9-deoxo-31-O-demethyl-FK506 and 9-deoxo-propyl-FK506 compounds, which are FK506 derivatives, are represented by the following formula (I), formula (II), formula (III) and formula (IV), respectively:

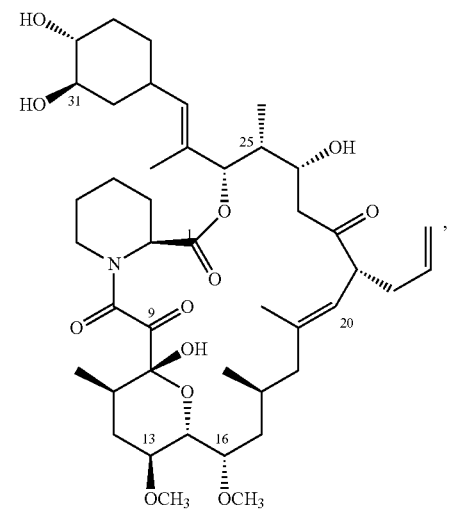

(I)

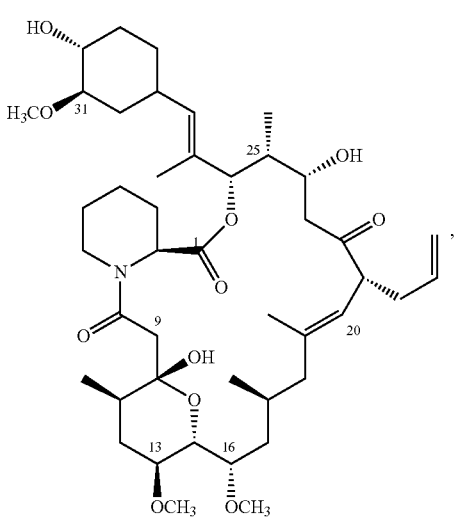

(II)

-continued

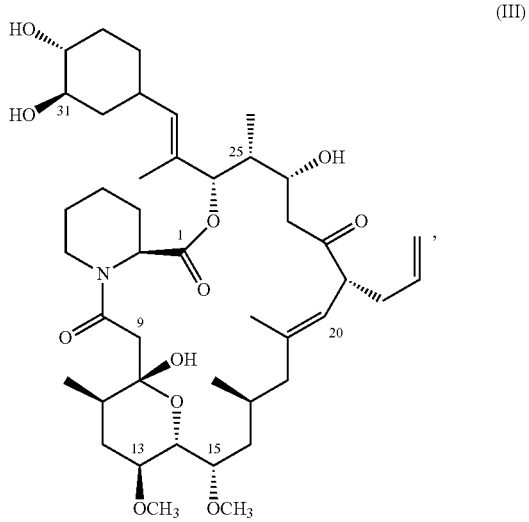

(III)

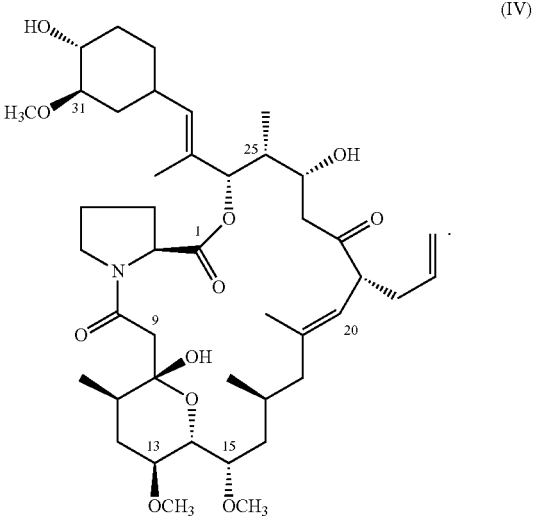

(IV)

As shown in FIGS. 1 and 2, all of 31-O-demethyl-FK506, 9 deoxo-FK506, 9-deoxo-31-O-demethyl-FK506 and 9-deoxo-propyl FK506 compounds, which are FK506 derivatives had inhibitory activity against *Cryptococcus neoformans*. Particularly, when 31-O-demethyl-FK506 and 9-deoxo-31-O-demethyl-FK506 were used at concentrations of 10 μg/ml and 40 μg/ml, they, showed large inhibition zones, indicating that the inhibitory activities of these FK506 derivatives increased as the concentrations thereof increased. Particularly, it was found that 31-O-demethyl-FK506 showed inhibitory activity higher than FK506.

FIG. 3 is a graph showing an increased or decreased change in the serum sensitivity of *Candida albicans* for 31-O-demethyl-FK506 that is FK506 derivative. Lower serum sensitivity with the passage of time indicates higher antifungal activity. As shown in FIG. 3, the inhibitory activity of 31-O-demethyl-FK506 against. *Candida albicans* was almost equal to that of FK506, and was very higher than that of the untreated control. Particularly, it could be seen that, from 6 hours after treatment, the FK506 derivative of the present invention maintained inhibitory activity higher than FK506.

INDUSTRIAL APPLICABILITY

As described above, the present invention provides a pharmaceutical composition for treating a fungal infection caused by a fungus of the genus *Cryptococcus* or a fungus of the genus *Candida*, the pharmaceutical composition containing FK506 derivative. The pharmaceutical composition has advantages in that it is harmless to the human body and has excellent antifungal effects.

The invention claimed is:

1. A method of treating a fungal infection caused by a fungus of the genus *Cryptococcus* or a fungus of the genus *Candida*, the method comprising administering to a subject in need thereof a composition comprising a therapeutically effective amount of Tacrolimus "FK506" derivative, wherein the Tacrolimus "FK506" derivative is selected from the group consisting of 31-O-demethyl-FK506, 9-deoxo-FK506, 9-deoxo-31-O-demethyl-FK506 and 9-deoxo-prolyl-FK506.

2. The method of claim 1, wherein the fungus of the genus *Cryptococcus* is *Cryptococcus neoformans*.

3. The method of claim 1, wherein the fungus of the genus *Candida* is *Candida albicans*.

4. An agent for treating a fungal infection caused by a fungus of the genus *Cryptococcus* or a fungus of the genus *Candida*, the agent comprising Tacrolimus "FK506" derivative selected from the group consisting of 31-O-demethyl-FK506, 9-deoxo-FK506, 9-demo-31-O-demethyl-FK506 and 9-deoxo-prolyl-FK506.

5. The agent of claim 4, wherein the fungus of the genus *Cryptococcus* is *Cryptococcus neoformans*.

6. The agent of claim 4, wherein the fungus of the genus *Candida* is *Candida albicans*.

* * * * *